(12) United States Patent
Numata

(10) Patent No.: US 8,177,860 B2
(45) Date of Patent: May 15, 2012

(54) OXIDATION HAIR DYE AND HAIR BLEACH

(75) Inventor: Chiho Numata, Saitama (JP)

(73) Assignee: Arimino Co., Ltd., Tokyo (JP)

( * ) Notice: Subject to any disclaimer, the term of this patent is extended or adjusted under 35 U.S.C. 154(b) by 0 days.

(21) Appl. No.: 12/992,481

(22) PCT Filed: Mar. 11, 2009

(86) PCT No.: PCT/JP2009/054608
§ 371 (c)(1),
(2), (4) Date: Jan. 31, 2011

(87) PCT Pub. No.: WO2009/113562
PCT Pub. Date: Sep. 17, 2009

(65) Prior Publication Data
US 2011/0182839 A1     Jul. 28, 2011

(30) Foreign Application Priority Data

Mar. 12, 2008 (JP) ................................ 2008-063384

(51) Int. Cl.
*A61Q 5/10* (2006.01)

(52) U.S. Cl. .......................... 8/405; 8/581; 8/607; 8/617

(58) Field of Classification Search .............. 8/405, 581, 8/607, 617
See application file for complete search history.

(56) References Cited

U.S. PATENT DOCUMENTS

| | | | |
|---|---|---|---|
| 6,485,528 B1 | 11/2002 | Bartels et al. | |
| 2001/0029636 A1 | 10/2001 | Brownbill et al. | |
| 2003/0145393 A1* | 8/2003 | Corbella et al. | 8/405 |
| 2007/0209124 A1* | 9/2007 | Bureiko et al. | 8/405 |
| 2007/0226916 A1 | 10/2007 | Mellul et al. | |

FOREIGN PATENT DOCUMENTS

| | | |
|---|---|---|
| JP | 63-035406 A | 2/1988 |
| JP | 11-349455 A | 12/1999 |
| JP | 2002-508304 A | 3/2002 |
| JP | 2003-516951 A | 5/2003 |
| JP | 2006-124279 A | 5/2006 |
| JP | 2007-015986 A | 1/2007 |
| JP | 2007-277236 A | 10/2007 |

OTHER PUBLICATIONS

International Search Report of PCT/JP2009/054608, mailing date Jun. 9, 2009.

* cited by examiner

*Primary Examiner* — Eisa Elhilo

(74) *Attorney, Agent, or Firm* — Westerman, Hattori, Daniels & Adrian, LLP

(57) ABSTRACT

Provided are an oxidation hair dye and a hair bleach, in particular, an oxidation hair dye and a hair bleach effective in use on dyed hair which has solved the problems in using oxidation hair dye or hair bleach, specifically problems such as hair showing a hard and unfavorable texture when treated by oxidation hair dye and hair bleach due to damage to the hair from those agents. An oxidation hair dye characterized by comprising ceramides and/or sterol esters, lecithin or a lecithin derivative and silicones.

5 Claims, No Drawings

OXIDATION HAIR DYE AND HAIR BLEACH

FIELD OF THE INVENTION

The present invention relates to an oxidation hair dye and hair bleach.

BACKGROUND ART

Conventionally, there have been problems such as hair showing a hard and unfavorable texture when treated with oxidation hair dye and hair bleach due to damage to the hair from those agents. Conventionally, this problem has been addressed with the application of conditioners or treatment agents such as pretreatment and/or post-treatment agents. In order to solve the above problem, for example, a hair-dying agent has been proposed which is characterized by the fact that it is a two-part hair-dying agent comprising a first agent which contains an oxidation dye intermediate and a second agent which contains an oxidizing agent, and that one or both of either the first or second agents contains egg yolk oil (laid-open patent H11-349455). Also, a hair color treatment agent has been proposed which is characterized by the fact that it is a treatment agent for hair coloring comprising a pretreatment agent and a post-treatment agent employed before and after a hair color treatment, that the pretreatment agent contains keratin hydrolysate and/or a derivative thereof, and the post-treatment agent contains at least one selected from the group made up of ceramide, a ceramide derivative, a phospholipid and a derivative of a phospholipid (laid-open patent 2002-322035). Additionally, the same document describes that the said hair color treatment further contains at least one selected from the group made up of plant-derived protein hydrolysate, a derivative of plant-derived protein hydrolysate, protein hydrolysate derived from egg whites and a derivative of protein hydrolysate derived from egg whites. However, issues arose for the above treatment agents wherein the agents were unable to sufficiently solve the problem and were sticky, and were unable to obtain a good hair texture.
Patented reference 1: Laid-Open Patent H11-349455
Patented reference 2: Laid-Open Patent 2002-322035

DISCLOSURE OF THE INVENTION

Problem to be Solved by the Invention

The present invention has as its object to provide an oxidation hair dye and hair bleach which has solved the problems in using oxidation hair dye or hair bleach, specifically problems such as hair showing a hard and unfavorable texture when treated by oxidation hair dye and hair bleach due to damage to the hair from those agents.

Means for Solving the Problem

When oxidation hair dye or hair bleach is employed in a treatment, in order to solve the above problem the inventors of the present invention have discovered that by using (1) ceramides and/or sterol esters, (2) lecithin or a lecithin derivative, and (3) silicones (hereafter, the three components (1)-(3) will simply be called the three components), and including these three components not in pretreatment and/or post-treatment agents but in the oxidation hair dye and hair bleach itself, for example including them in the oxidation hair dye or hair bleach itself which is comprised of a first and second agent, and by including the three components at specific content amounts, the feel when washing hair after coloring (bleaching) is better, treated texture (smoothness, softness) is good, there is shine, and they persist, and in addition that the "look of the color" of the hair after treatment is also good, thus arrived at the present invention. In particular, oxidation hair dye containing the three components described previously had shine and good treated texture (smoothness, softness), and the "look of the color" of the treated hair was also good, and these effects were expressed even more effectively when the oxidation hair dye of the present invention was used in the dying of dyed hair.

For the oxidation hair dye employed in the present invention, we can make broad use of known oxidation hair dyes, including for example a two-part agent comprising a first agent which contains an oxidation dye intermediate and a second agent which contains an oxidizing agent. The hair bleach employed in the present invention may also make broad use of known hair bleaches, including for example a powder bleach which is composed of a two-part agent comprising a first agent which is comprised of persulfate, alkaline agents (powdered agents, such as sodium silicate), thickeners, diluents and so on and a second agent which is comprised of hydrogen peroxide solution, surfactants and so on, or a two-part agent bleach which is composed of a first agent comprising alkaline agents, surfactants, and so on, and a second agent comprising hydrogen peroxide solution, surfactants, and so on.

In the two agent composition oxidation hair dye or hair bleach, the three components described previously may be included in either of the first agent or second agent, or in both agents (in examples 1 through 22, the three components are included in the first agent; in example 23, the three components are included in the second agent). In order to achieve the previously described results, the content amounts of these three components are a ceramides and/or sterol esters content amount of usually 0.005 to 2.5% by weight of the total weight of oxidation hair dye or hair bleach, preferably 0.025 to 1.5% by weight, more preferably 0.05 to 1% by weight, a lecithin or lecithin derivative content amount of usually 0.005 to 1.5% by weight, preferably 0.025 to 1% by weight, more preferably 0.05 to 0.5% by weight, and a silicones content amount of usually 0.025 to 5.0% by weight, preferably 0.05 to 2.5% by weight, more preferably 0.1 to 1.5% by weight. However, the oxidation hair dye or hair bleach employed in the present invention is not limited to two parts, but may also employ compositions of more than two parts, for example a three-part agent composition. Additionally, the three components may also be included in acidic hair dyes other than oxidation hair dye or hair bleach.

The ceramides employed in the present invention include ceramide and its derivatives. For these ceramides and their derivatives, sphingolipids which make up approximately 50% of the intercellular lipids of the human horny cell layer (ceramides which exist in the human horny cell layer include for example the structures of ceramides 1 through 7 below), rice bran glucosphingolipids obtained by extraction and refining from rice bran (rice germ) which is a type of plant ceramide, phytosphingosine which is a ceramide precursor and is plentiful in plant ceramides, N-stearoyloxy heptacosanoyl phytosphingosine, N-stearoyl sphingosine, N-stearoyl phytosphingosine, N-oleoyl phytosphingosine, N-2-hydroxystearoyl phytosphingosine, and so on may be named.

[Formula 1]
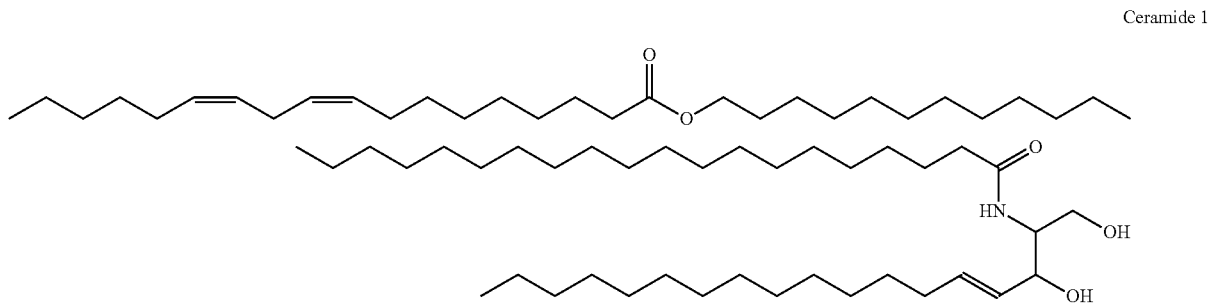
Ceramide 1
[Formula 2]
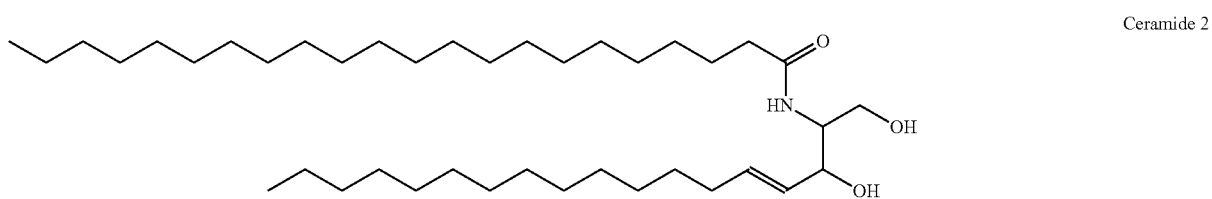
Ceramide 2
[Formula 3]
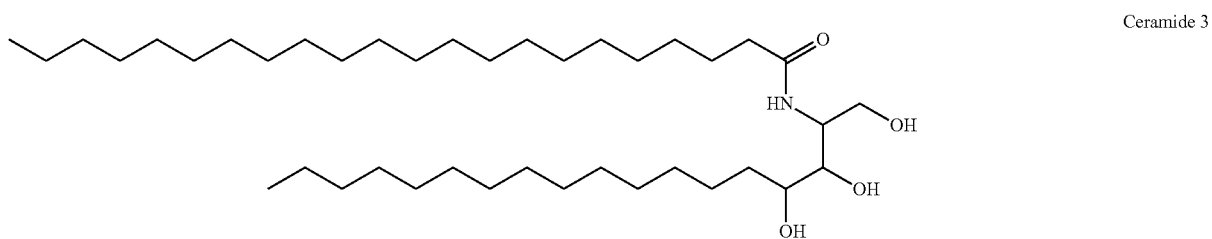
Ceramide 3
[Formula 4]
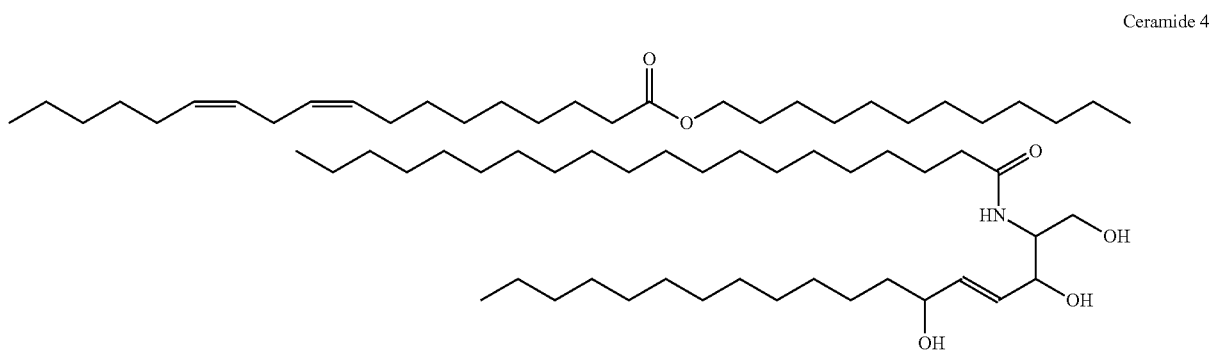
Ceramide 4
[Formula 5]
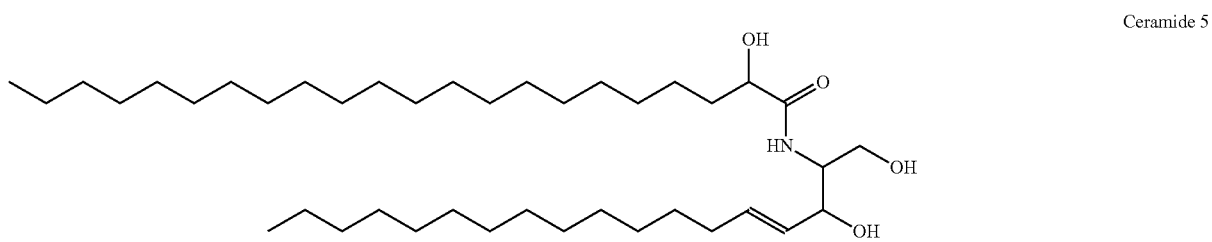
Ceramide 5

[Formula 6]

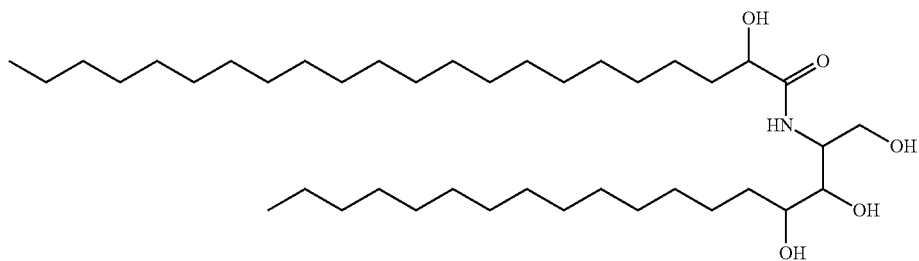

Ceramide 6

[Formula 7]

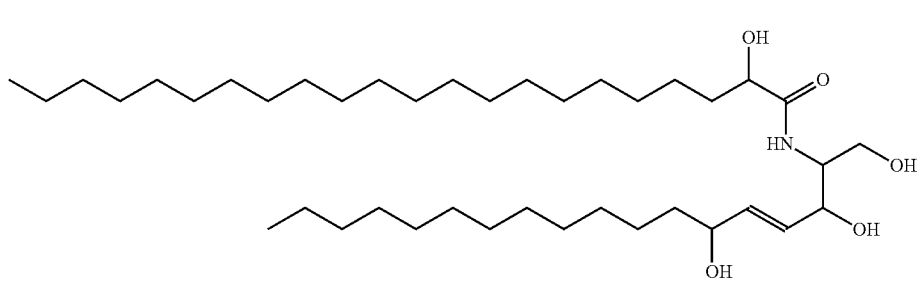

Ceramide 7

Additionally, as a substance which can achieve similar results to ceramides, in the present invention sterol esters may be employed in place of the ceramides described above, or alongside the ceramides described above. These sterol esters include for example cholesteryl acetate, cholesteryl nonanoate, cholesteryl stearate, cholesteryl isostearate, cholesteryl oleate, phytosteryl oleate, N-lauroyl-L-glutamate di(cholesteryl/behenyl/octyldodecyl), N-lauroyl-L-glutamate di(cholesteryl/octyldodecyl), N-lauroyl-L-glutamate di(phytosteryl/behenyl/octyldodecyl), N-lauroyl-L-glutamate di(phytosteryl/octyldodecyl), cholesteryl 12-hydroxystearate, phytosteryl 12-hydroxystearate, macadamia nut oil fatty acid cholesteryl, macadamia nut oil fatty acid phytosteryl, phytosteryl isostearate, soft lanolin fatty acid cholesteryl, hard lanolin fatty acid cholesteryl, long-chain branching fatty acid cholesteryl, long chain α-hydroxy fatty acid cholesteryl, and so on.

Among these sterol esters, N-lauroyl-L-glutamate di(cholesteryl/behenyl/octyldodecyl), N-lauroyl-L-glutamate di(cholesteryl/octyldodecyl), N-lauroyl-L-glutamate di(phytosteryl/behenyl/octyldodecyl), N-lauroyl-L-glutamate di(phytosteryl/octyldodecyl), soft lanolin fatty acid cholesteryl, hard lanolin fatty acid cholesteryl, long chain branching fatty acid cholesteryl, long chain α-hydroxy fatty acid cholesteryl, and so on are preferable from the standpoint of adequate softness of treated hair.

The lecithin employed in the present invention indicates a lipid preparation containing phospholipids, and includes as raw materials, for example, "egg yolk lecithin" which takes egg yolks as its raw material, "soy lecithin" which takes soy as its raw material, such as hydrogenated soy lecithin, and so on. Also, for the silicones employed in the present invention, silicone which is employed as a raw material for ordinary make-up may be used. This sort of silicone includes dimethyl silicone, amine-modified silicone, high polymerization silicone, and so on. Also, components employed in ordinary oxidation hair dye and hair bleach may be contained in the oxidation hair dye and hair bleach of the present invention, as necessary.

Effect of the Invention

The invention was able to provide an oxidation hair dye and hair bleach which solved problems such as hair showing a hard and unfavorable texture when treated with oxidation hair dye and hair bleach due to damage to the hair from those agents.

BEST MODE FOR CARRYING OUT THE INVENTION

Examples 1 Through 22 and Comparative Examples 1 Through 7

On a bundle of Beaulax-brand hair (BS-B3A) a twenty-minute bleach treatment using ordinary bleach was performed. The bundle of hair to which no treatment was applied is A and the bundle of hair which was treated as described above is B. A hair dye or hair bleach which mixed a first agent composed with the formulations of Tables 1 through 4 below and a second agent which is shown by the formulation of Table 5 at a 1:1 ratio was used, was left to sit for twenty minutes after applying to the hair, and was washed clean with shampoo in common use. A conditioner was then applied and washed out, then the hair was fully dried with a hairdryer. The results are shown below.

TABLE 1

| | Hair Color First Agent Formulation | Example 1 | Example 2 | Example 3 | Example 4 | Example 5 | Example 6 | Example 7 |
|---|---|---|---|---|---|---|---|---|
| FOR-MU- | cetostearyl alcohol | 9.00 | ← | ← | ← | ← | ← | ← |
| | paraffin | 5.00 | ← | ← | ← | ← | ← | ← |

TABLE 1-continued

| | Hair Color First Agent Formulation | Example 1 | Example 2 | Example 3 | Example 4 | Example 5 | Example 6 | Example 7 |
|---|---|---|---|---|---|---|---|---|
| LA-TION | lanolin fatty acid octyldodecyl | 5.00 | ← | ← | ← | ← | ← | ← |
| | N-lauroyl-L-glutamate di(phytosteryl/octyldodecyl) | 0.01 | 0.05 | 0.10 | 2.00 | 2.00 | 3.00 | 5.00 |
| | glycerin | 5.00 | ← | ← | ← | ← | ← | ← |
| | polyoxyethelene cetyl ether | 7.00 | ← | ← | ← | ← | ← | ← |
| | cetostearyl trimethyl ammonium | 2.00 | ← | ← | ← | ← | ← | ← |
| | hydrogenated soy lecithin | 0.10 | 0.10 | 0.10 | 0.10 | 1.00 | 0.10 | 0.10 |
| | (aminoethyl aminopropyl methicone/dimethicone) copolymer | 0.20 | 0.20 | 0.20 | 0.20 | 3.00 | 0.20 | 0.20 |
| | 28% ammonium hydrate | 5.00 | ← | ← | ← | ← | ← | ← |
| | sodium sulfite | 0.50 | ← | ← | ← | ← | ← | ← |
| | paraphenylenediamine | 0.10 | ← | ← | ← | ← | ← | ← |
| | resorcinol | 0.08 | ← | ← | ← | ← | ← | ← |
| | meta aminophenol | 0.05 | ← | ← | ← | ← | ← | ← |
| | purified water | appropriate amount | ← | ← | ← | ← | ← | ← |
| | total amount | 100.00 | ← | ← | ← | ← | ← | ← |
| RAT-ING | feel of hair during washing | ○ | ◎ | ◎ | ◎ | ◎ | ○ | △ |
| | treated shine | ○ | ◎ | ◎ | ◎ | ◎ | ◎ | ◎ |
| | treated smoothness | ○ | ○ | ◎ | ◎ | ◎ | ◎ | ◎ |
| | treated softness | △ | ○ | ◎ | ◎ | ◎ | ◎ | ◎ |
| | look of the color | ○ | ◎ | ◎ | ◎ | ◎ | ◎ | ◎ |
| | persistence | ○ | ○ | ◎ | ◎ | ◎ | ◎ | ◎ |

In the table, ← indicates that the amount contained is the same amount shown in the column to the left.

TABLE 2

| | Hair Color First Agent Formulation | Example 8 | Example 9 | Example 10 | Example 11 | Example 12 | Example 13 | Example 14 |
|---|---|---|---|---|---|---|---|---|
| FOR-MU-LA-TION | cetostearyl alcohol | 9.00 | ← | ← | ← | ← | ← | ← |
| | paraffin | 5.00 | ← | ← | ← | ← | ← | ← |
| | lanolin fatty acid octyldodecyl | 5.00 | ← | ← | ← | ← | ← | ← |
| | N-lauroyl-L-glutamate di(phytosteryl/octyldodecyl) | 0.10 | 0.10 | 0.10 | 0.10 | 0.10 | 0.10 | 0.10 |
| | glycerin | 5.00 | ← | ← | ← | ← | ← | ← |
| | polyoxyethelene cetyl ether | 7.00 | ← | ← | ← | ← | ← | ← |
| | cetostearyl trimethyl ammonium | 2.00 | ← | ← | ← | ← | ← | ← |
| | hydrogenated soy lecithin | 0.01 | 0.05 | 1.00 | 2.00 | 3.00 | 0.10 | 0.10 |
| | (aminoethyl aminopropyl methicone/dimethicone) copolymer | 0.20 | 0.20 | 0.20 | 0.20 | 0.20 | 0.05 | 0.10 |
| | 28% ammonium hydrate | 5.00 | ← | ← | ← | ← | ← | ← |
| | sodium sulfite | 0.50 | ← | ← | ← | ← | ← | ← |
| | paraphenylenediamine | 0.10 | ← | ← | ← | ← | ← | ← |
| | resorcinol | 0.08 | ← | ← | ← | ← | ← | ← |
| | meta aminophenol | 0.05 | ← | ← | ← | ← | ← | ← |
| | purified water | appropriate amount | ← | ← | ← | ← | ← | ← |
| | total amount | 100.00 | ← | ← | ← | ← | ← | ← |
| RAT-ING | feel of hair during washing | ○ | ◎ | ◎ | ◎ | ○ | ◎ | ◎ |
| | treated shine | ◎ | ◎ | ◎ | ○ | △ | ○ | ○ |
| | treated smoothness | △ | ○ | ◎ | ◎ | ○ | △ | ○ |
| | treated softness | △ | ○ | ◎ | ◎ | ○ | ○ | ◎ |
| | look of the color | ○ | ◎ | ◎ | ◎ | ○ | ○ | ◎ |
| | persistence | ○ | ○ | ◎ | ◎ | ◎ | △ | ○ |

TABLE 3

| Hair Color First Agent Formulation | | Example 15 | Example 16 | Example 17 | Example 18 | Example 19 | Example 20 | Example 21 | Example 22 |
|---|---|---|---|---|---|---|---|---|---|
| FORMULATION | cetostearyl alcohol | 9.00 | ← | ← | ← | ← | ← | ← | ← |
| | paraffin | 5.00 | ← | ← | ← | ← | ← | ← | ← |
| | lanolin fatty acid octyldodecyl | 5.00 | ← | ← | ← | ← | ← | ← | ← |
| | N-lauroyl-L-glutamate di(phytosteryl/octyldodecyl) | 0.10 | 0.10 | 0.10 | 0.01 | 0.10 | — | 0.10 | 0.10 |
| | (2S,3R)-2-octadecanoyl amino-octadecane-1,3-diol | — | — | — | — | — | 0.10 | 0.10 | — |
| | glycerin | 5.00 | ← | ← | ← | ← | ← | ← | ← |
| | polyoxyethelene cetyl ether | 7.00 | ← | ← | ← | ← | ← | ← | ← |
| | cetostearyl trimethyl ammonium | 2.00 | ← | ← | ← | ← | ← | ← | ← |
| | hydrogenated soy lecithin | 0.10 | 0.10 | 0.10 | 0.01 | 0.10 | 0.10 | 0.10 | 0.10 |
| | (aminoethyl aminopropyl methicone/dimethicone) copolymer | 3.00 | 5.00 | 10.00 | 0.05 | 0.20 | 0.20 | 0.20 | — |
| | high polymerization methyl polysiloxane | — | — | — | — | — | — | — | 0.20 |
| | 28% ammonium hydrate | 5.00 | ← | ← | ← | ← | ← | ← | ← |
| | sodium sulfite | 0.50 | ← | ← | ← | ← | ← | ← | ← |
| | paraphenylenediamine | 0.10 | ← | ← | ← | — | 0.10 | ← | ← |
| | resorcinol | 0.08 | ← | ← | ← | — | 0.08 | ← | ← |
| | meta aminophenol | 0.05 | ← | ← | ← | — | 0.05 | ← | ← |
| | purified water | appropriate amount | ← | ← | ← | ← | ← | ← | ← |
| | total amount | 100.00 | ← | ← | ← | ← | ← | ← | ← |
| RATING | feel of hair during washing | ◎ | ○ | ○ | ○ | ◎ | ◎ | ◎ | ◎ |
| | treated shine | ◎ | ◎ | ◎ | ○ | ◎ | ◎ | ◎ | ◎ |
| | treated smoothness | ◎ | ◎ | ◎ | Δ | ◎ | ◎ | ◎ | ◎ |
| | treated softness | ◎ | ○ | Δ | Δ | ◎ | ◎ | ◎ | ◎ |
| | look of the color | ◎ | ◎ | ◎ | ○ | ◎ | ◎ | ◎ | ◎ |
| | persistence | ◎ | ◎ | ◎ | Δ | ◎ | ◎ | ◎ | ◎ |

In the preceding table, (2S,3R)-2-octadecanoyl amino-octadecane-1,3-diol is a substance equivalent to ceramide 2.

TABLE 4

| Hair Color First Agent Formulation | | Comp. Example 1 | Comp. Example 2 | Comp. Example 3 | Comp. Example 4 | Comp. Example 5 | Comp. Example 6 | Comp. Example 7 | Comp. Example 8 |
|---|---|---|---|---|---|---|---|---|---|
| FORMULATION | cetostearyl alcohol | 9.00 | ← | ← | ← | ← | ← | ← | ← |
| | paraffin | 5.00 | ← | ← | ← | ← | ← | ← | ← |
| | lanolin fatty acid octyldodecyl | 5.00 | ← | ← | ← | ← | ← | ← | ← |
| | N-lauroyl-L-glutamate di(phytosteryl/octyldodecyl) | — | 7.00 | 0.10 | 0.10 | 0.10 | 0.10 | — | — |
| | glycerin | 5.00 | ← | ← | ← | ← | ← | ← | ← |
| | polyoxyethelene cetyl ether | 7.00 | ← | ← | ← | ← | ← | ← | ← |
| | cetostearyl trimethyl ammonium | 2.00 | ← | ← | ← | ← | ← | ← | ← |
| | hydrogenated soy lecithin | 0.10 | 0.10 | — | 4.00 | 0.10 | 0.10 | — | — |
| | (aminoethyl aminopropyl methicone/dimethicone) copolymer | 0.20 | 0.20 | 0.20 | 0.20 | — | 12.00 | — | — |
| | 28% ammonium hydrate | 5.00 | ← | ← | ← | ← | ← | ← | ← |
| | sodium sulfite | 0.50 | ← | ← | ← | ← | ← | ← | ← |
| | paraphenylenediamine | 0.10 | ← | ← | ← | ← | ← | — | 0.10 |
| | resorcinol | 0.08 | ← | ← | ← | ← | ← | — | 0.08 |
| | meta aminophenol | 0.05 | ← | ← | ← | ← | ← | — | 0.05 |
| | purified water | appropriate amount | ← | ← | ← | ← | ← | ← | ← |
| | total amount | 100.00 | ← | ← | ← | ← | ← | ← | ← |
| RATING | feel of hair during washing | Δ | X | Δ | Δ | ○ | Δ | X | X |
| | treated shine | Δ | ◎ | ○ | X | Δ | ◎ | X | Δ |

TABLE 4-continued

| Hair Color First Agent Formulation | Comp. Example 1 | Comp. Example 2 | Comp. Example 3 | Comp. Example 4 | Comp. Example 5 | Comp. Example 6 | Comp. Example 7 | Comp. Example 8 |
|---|---|---|---|---|---|---|---|---|
| treated smoothness | ○ | ⊚ | X | Δ | X | X | X | X |
| treated softness | X | ○ | X | ○ | Δ | X | X | X |
| look of the color | Δ | ⊚ | Δ | Δ | Δ | ⊚ | X | X |
| persistence | ○ | ⊚ | Δ | ⊚ | X | ⊚ | X | X |

TABLE 5

| | Hair Color Second Agent Formulation | |
|---|---|---|
| FORMULATION | cetanol | 4.00 |
| | paraffin | 1.00 |
| | polyoxyethylene cetyl ether | 1.50 |
| | cetostearyl trimethyl ammonium | 0.50 |
| | phenacetin | 0.10 |
| | hydroxyethane diphosphonic acid 4 sodium | 0.05 |
| | phosphoric acid | 0.05 |
| | hydrogen peroxide | 6.00 |
| | purified water | appropriate amount |
| | total amount | 100.00 |

Example 23

Other than employing the formulation of the hair color first agent shown in Table 6 below and the formulation of the hair color second agent shown in Table 7 below, we performed a treatment on hair similar to the preceding Examples 1 through 22 and Comparative Examples 1 through 7.

TABLE 6

| | Hair Color First Agent Formulation | |
|---|---|---|
| | cetostearyl alcohol | 9.00 |
| | paraffin | 5.00 |
| | lanolin fatty acid octyldodecyl | 5.00 |
| | glycerin | 5.00 |
| | polyoxyethylene cetyl ether | 7.00 |
| | cetostearyl trimethyl ammonium | 2.00 |
| | 28% ammonium hydrate | 5.00 |
| | sodium sulfite | 0.50 |
| | paraphenylenediamine | 0.10 |
| | resorcinol | 0.08 |
| | meta aminophenol | 0.05 |
| | purified water | appropriate amount |
| | total amount | 100.00 |

TABLE 7

| | Hair Color Second Agent Formulation | Example 23 |
|---|---|---|
| FORMULATION | cetanol | 4.00 |
| | paraffin | 1.00 |
| | N-lauroyl-L-glutamate di(phytosteryl/octyldodecyl) | 0.10 |
| | polyoxyethylene cetyl ether | 1.50 |
| | cetostearyl trimethyl ammonium | 0.50 |
| | hydrogenated soy lecithin | 0.10 |
| | (aminoethyl aminopropyl methicone/dimethicone) copolymer | 0.20 |
| | phenacetin | 0.10 |
| | hydroxyethane diphosphonic acid 4 sodium | 0.05 |

TABLE 7-continued

| | Hair Color Second Agent Formulation | Example 23 |
|---|---|---|
| | phosphoric acid | 0.05 |
| | hydrogen peroxide | 6.00 |
| | purified water | appropriate amount |
| | total amount | 100.00 |
| RATING | feel of hair during washing | ⊚ |
| | treated shine | ⊚ |
| | treated smoothness | ⊚ |
| | treated softness | ⊚ |
| | look of the color | ⊚ |
| | persistence | ⊚ |

The ratings of the preceding Tables 1 through 4 and Table 7 were made by a panel of professionals (beauticians) with the following rating criteria.

Rating Criteria

1. Feel of Hair During Washing

The hair dye or hair bleach of Examples 1 through 23 and of Comparative Examples 1 through 7 was applied to a bundle of hair A, then after being left to sit for twenty minutes, the feel of the bundle of hair when washing it with shampoo in common use was rated.

Rating Criteria

⊚: feel is extremely good

○: feel is good

Δ: feel is slightly good

X: feel is bad, notice tugging

2. Treated Shine

After washing the bundle of hair clean, the conditioning agent (1) shown in Table 8 below was applied then washed out and the shine was rated after completely drying the hair with a hairdryer.

Rating Criteria

⊚: extremely shiny

○: shiny

Δ: slightly shiny

X: no shine, looks dry and damaged.

TABLE 8

| Conditioning Agent Formulation | (1) | (2) |
|---|---|---|
| cetostearyl alcohol | 5.00 | 5.00 |
| behenyl alcohol | 1.00 | 1.00 |
| cetyl octanoate | 2.50 | 2.50 |
| N-lauroyl-L-glutamate di(phytosteryl/octyldodecyl) | — | 0.10 |
| glycerin | 3.00 | 3.00 |
| cetostearyl trimethyl ammonium | 5.00 | 5.00 |
| hydrogenated soy lecithin | — | 0.10 |
| (aminoethyl aminopropyl methicone/dimethicone) copolymer | — | 0.20 |

TABLE 8-continued

| Conditioning Agent Formulation | (1) | (2) |
| --- | --- | --- |
| citrate | 0.05 | 0.05 |
| Na citrate | 0.02 | 0.02 |
| paraben | 0.40 | 0.40 |
| purified water | appropriate amount | appropriate amount |
| total amount | 100.00 | 100.00 |

3. Treated Smoothness

The smoothness of the previously-described bundle of hair was rated.

Rating Criteria
◎: extremely smooth
○: smooth
Δ: slightly smooth
X: feels squeaky 4. Treated Softness The softness of the previously-described bundle of hair was rated.

Rating Criteria
◎: extremely soft
○: soft
Δ: slightly soft
X: feel of stiffness

5. Look of the Color

The look of the color of the previously-described bundle of hair was rated.

Rating Criteria
◎: deeply dyed the color, looks clean
○: dyed the color, looks clean
Δ: slightly dyed the color, looks clean
X: color looks faded.

6. Persistence

To what degree the results of each of the above rated items persisted was rated.

Rating Criteria
◎: results of each of the rated items persists more than one month
○: results of each of the rated items persists one month
Δ: results of each of the rated items persists two weeks
X: results of each of the rated items do not persist Comparative Example 8

We applied hair dye which mixed 1:1 the first agent of Comparative Example 8 and the second agent of Table 5, then after being left to sit for twenty minutes it was washed clean with shampoo in common use. We then applied conditioning agent (2) from the preceding Table 8 then washed it out and dried the hair completely with a hairdryer. The rating criteria were carried out similarly to the previously described rating criteria 1 through 6.

Example 24

We applied each hair dye which mixed 1:1 each of the first agents of Example 3 and Comparative Example 8 with the second agent of Table 5 to bundle of hair A, then after being left to sit for twenty minutes it was washed clean with shampoo in common use. We then applied conditioning agent (1) shown in the preceding Table 8 and washed it out and dried the hair completely with a hairdryer.

Example 25

We applied each hair dye which mixed 1:1 each of the first agents of Example 3 and Comparative Example 8 with the second agent of Table 5 to bundle of hair B, then after being left to sit for twenty minutes it was washed clean with shampoo in common use. We then applied conditioning agent (1) shown in the preceding Table 8 and washed it out and dried the hair completely with a hairdryer.

Rating Criteria

1. Feel of Hair During Washing

When hair dye was applied to a bundle of hair, then after being left to sit for twenty minutes was washed clean with shampoo in common use, to what degree the rated results of Example 3 improved over the rated results of Comparative Example 8 for the feel of the hair was rated.

Rating Criteria
5: feel is extremely improved
4: feel is improved
3: feel is slightly improved
2: feel is the same
1: feel is worse 2. Treated Shine After the previously described bundle of hair was washed, then conditioning agent (1) shown in the preceding Table 8 was applied and washed out and it was dried completely with a hairdryer, to what degree the rated results of Example 3 improved over the rated results of Comparative Example 8 for the shine was rated.

Rating Criteria
5: shine is extremely improved
4: shine is improved
3: shine is slightly improved
2: shine is the same
1: shine is worse 3. Treated Smoothness To what degree the rated results of Example 3 improved over the rated results of Comparative Example 8 for the smoothness of the previously described bundle of hair was rated.

Rating Criteria
5: smoothness is extremely improved
4: smoothness is improved
3: smoothness is slightly improved
2: smoothness is the same
1: smoothness is worse 4. Treated Softness To what degree the rated results of Example 3 improved over the rated results of Comparative Example 8 for the softness of the previously described bundle of hair was rated.

Rating Criteria
5: softness is extremely improved
4: softness is improved
3: softness is slightly improved
2: softness is the same
1: softness is worse 5. Look of the Color To what degree the rated results of Example 3 improved over the rated results of Comparative Example 8 for the look of the color of the previously described bundle of hair was rated.

Rating Criteria
5: look of the color is extremely improved
4: look of the color is improved
3: look of the color is slightly improved
2: look of the color is the same
1: look of the color is worse 6. Persistence To what degree the rated results of Example 3 improved over the rated results of Comparative Example 8 was rated for the degree to which the results of each of the previously described rated items persisted.

Rating Criteria
  5: persistence is extremely improved
  4: persistence is improved
  3: persistence is slightly improved
  2: persistence is the same
  1: persistence is worse The rated results of the previously described rated items made with the rating criteria of previously described Examples 24 and 25 are shown in Table 9, below.

TABLE 9

|  |  | Example 24 | Example 25 |
|---|---|---|---|
| RATING | Feel of Hair during Washing | 4 | 4 |
|  | Treated Shine | 4 | 5 |
|  | Treated Smoothness | 4 | 4 |
|  | Treated Softness | 5 | 5 |
|  | Look of the Color | 4 | 5 |
|  | Persistence | 4 | 5 |

The invention claimed is:

1. An oxidation hair dye containing at least 0.005 to 2.5% by weight of ceramides and/or sterol esters, 0.005 to 1.5% by weight of lecithin or a lecithin derivative, and 0.025 to 5% by weight of silicones.

2. A hair bleach containing at least 0.005 to 2.5% by weight of ceramides and/or sterol esters, 0.005 to 1.5% by weight of lecithin or a lecithin derivative, and 0.025 to 5% by weight of silicones.

3. The oxidation hair dye, according to claim 1, characterized in that it is employed on dyed hair.

4. A method for dying hair comprising treating hair with the oxidation hair dye of claim 1.

5. A method for bleaching hair comprising treating hair with the hair bleach of claim 2.

* * * * *